(12) United States Patent
Daughton et al.

(10) Patent No.: US 11,901,076 B1
(45) Date of Patent: Feb. 13, 2024

(54) PREDICTION OF PROBABILITY DISTRIBUTION FUNCTION OF CLASSIFIERS

(71) Applicant: Curemetrix, Inc., San Diego, CA (US)

(72) Inventors: William Scott Daughton, Los Alamos, NM (US); Chi Yung Chim, La Jolla, CA (US); Junhao Wang, Setauket, NY (US); Homayoun Karimabadi, Del Mar, CA (US)

(73) Assignee: CureMetrix, Inc., San Diego, CA (US)

( * ) Notice: Subject to any disclaimer, the term of this patent is extended or adjusted under 35 U.S.C. 154(b) by 410 days.

(21) Appl. No.: 17/346,181

(22) Filed: Jun. 11, 2021

Related U.S. Application Data

(60) Provisional application No. 63/038,685, filed on Jun. 12, 2020.

(51) Int. Cl.
*G16H 50/20* (2018.01)
*G16H 10/60* (2018.01)
*G16H 30/20* (2018.01)
*G06T 7/00* (2017.01)
*G16H 50/30* (2018.01)

(52) U.S. Cl.
CPC ........... *G16H 50/20* (2018.01); *G06T 7/0012* (2013.01); *G16H 10/60* (2018.01); *G16H 30/20* (2018.01); *G16H 50/30* (2018.01); *G06T 2207/20076* (2013.01); *G06T 2207/30068* (2013.01); *G06T 2207/30096* (2013.01)

(58) Field of Classification Search
CPC ........ G16H 50/20; G16H 10/60; G16H 30/20; G16H 50/30; G06T 7/0012; G06T 2207/20076; G06T 2207/30068; G06T 2207/30096
USPC .......................................................... 382/128
See application file for complete search history.

(56) References Cited

U.S. PATENT DOCUMENTS

2006/0269111 A1* 11/2006 Stoecker ................. G16H 30/40
382/128
2020/0372636 A1* 11/2020 Ha ............................. G06T 5/50
2020/0395123 A1* 12/2020 Akselrod-Ballin ...... G06N 3/02
2023/0071400 A1* 3/2023 Abdolell ................. G16H 30/20

* cited by examiner

*Primary Examiner* — Charlotte M Baker
(74) *Attorney, Agent, or Firm* — Cooley LLP

(57) ABSTRACT

During operation, a computer system may apply a pretrained predictive model to information for at least a subset of a plurality of individuals, and may determine levels of uncertainty in results of the pretrained predictive model for at least the subset of the plurality of individuals. Then, the computer system may dynamically adapt a at least one threshold range based at least in part on the determined levels of uncertainty and a predefined target performance of the pretrained predictive model for the plurality of individuals. Next, the computer system may perform different remedial actions for a first group of individuals in the plurality of individuals having the results where the levels of uncertainty are within the at least one threshold range and a second group of individuals in the plurality of individuals having the results where the levels of uncertainty are outside of the at least one threshold range.

20 Claims, 15 Drawing Sheets

 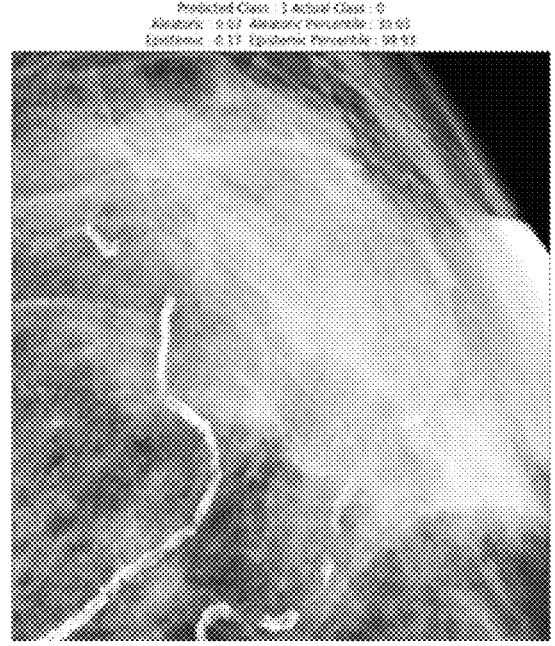
FIG. 7A  FIG. 7B
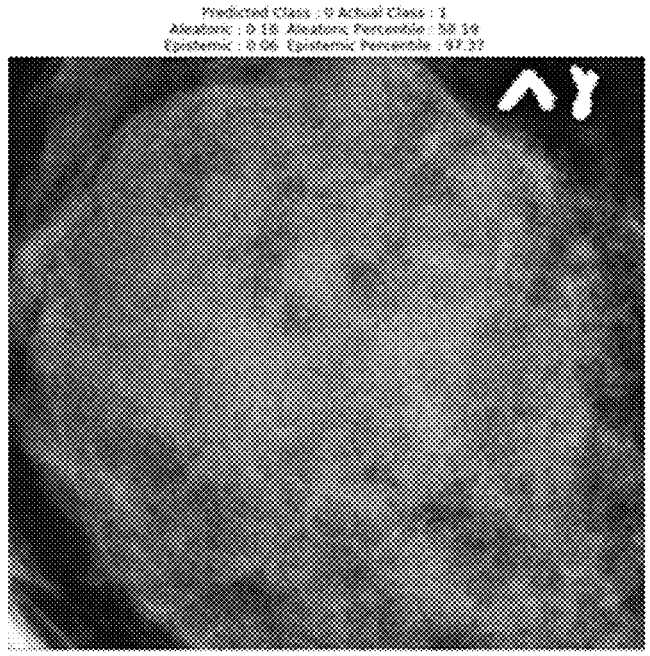
FIG. 7C

PREDICTION OF PROBABILITY DISTRIBUTION FUNCTION OF CLASSIFIERS

CROSS-REFERENCE TO RELATED APPLICATIONS

This application claims priority under 35 U.S.C. 119(e) to U.S. Provisional Application Ser. No. 63/038,685, entitled "Prediction of Probability Distribution Function Classifiers," by Daughton et al., filed on Jun. 12, 2020, the contents of which are herein incorporated by reference.

STATEMENT REGARDING FEDERALLY SPONSORED RESEARCH OR DEVELOPMENT

Not Applicable.

FIELD

The invention relates to deep neural networks in the analysis of medical images and other complex data sets to aid medical professionals in determining uncertainty levels of the analysis.

INTRODUCTION

Rapid advances in technology have led to a proliferation of data. Techniques used to generate, collect and process data involve machine learning (ML)/artificial intelligence (AI)-based systems and methods. ML/AI-based systems apply deep neural networks (DNN) for: (i) computer vision (e.g., anomaly detection, classification, segmentation); (ii) time series prediction and forecasting; (iii) speech recognition; and (iv) natural language processing (NLP).

However, a shortcoming of DNN is that when faced with examples coming from a different distribution than the training data, the DNN generates the wrong predictions, with high confidence. This is attributed to the inability of the DNN-derived models to quantify and output its uncertainty in each instance. An illustrative example is when a DNN is: (i) trained to identify cancerous lesions in mammography and (ii) given an image with microcalcifications. The DNN-derived model is forced to classify the image as either cancerous lesion or normal, while having no way of expressing the uncertainty due to the fact that the training set of DNN-derived model has not seen examples of microcalcifications. High uncertainty output is akin to saying "I am not sure".

The above is an example of uncertainty which arises from limitations in the training set. Another source of uncertainty is from: (i) variance in the data or (ii) the underlying process. An instance of this in mammography is where even images taken of the same patient a few minutes apart are not identical due to positioning of the patient and the compression of the breast.

SUMMARY

A first group of embodiments include a computer-implemented method for assessing uncertainties. The method involves: applying the trained model on the plurality of cases; determining a level of uncertainty in the plurality of cases; wherein the level of uncertainty is with a predetermined range, wherein the predetermined range is between a lower acceptable limit and higher acceptable limit; in response to determining the level of uncertainty in the plurality of cases is within the predetermined range, implementing a first solution; and in response to determining the level of uncertainty in the plurality of cases is outside a predetermined range, implementing at least one additional solution.

In accordance with an aspect, in response to determining the level of uncertainty in the plurality of cases is outside the predetermined range, a second solution is implemented.

In accordance with an aspect, implementing the first solution comprises generating protocols for one or more cases where the level of uncertainty is within the predetermined range; sending the one or more cases where the level of uncertainty is within the predetermined range to a bucket for cases where the level of uncertainty is low; and in response to sending the one or more cases where the level of uncertainty is within the predetermined range to the bucket for cases where the level of uncertainty is low, validating the model.

In accordance with an aspect, implementing the second solution includes generating protocols for one or more cases where the level of uncertainty outside the predetermined range; creating a bucket for cases where the level of uncertainty is high; identifying one or more cases where the level of uncertainty is high; in response to identifying the one or more cases where the level of uncertainty is high, sending the one or more cases where the level of uncertainty is high to the bucket for cases where the level of uncertainty is high; increasing an efficacy of the model by decreasing one or more of aleaotoric uncertainty and epistemic uncertainty; and generating a score, wherein the score accounts for a mean and a distribution function.

In accordance with an aspect, training the model involves modifying the model by developing a training strategy and thereby reducing the level of uncertainty.

In accordance with an aspect, the plurality of cases is selected from the group consisting of image data, text data, and any combination thereof.

In accordance with an aspect, training the model involves modifying the model by developing a training strategy. Thereby, the level of uncertainty is reduced.

In accordance with an aspect, the image data includes images interpreted according to BI-RADS and images examined for microcalcifications, breast arterial calcifications (BAC), and lesions.

In accordance with an aspect, implementing the first solution and the additional solution occurs in a triage setting and an auto-populating setting for reporting an assessment each case of the plurality of cases.

In accordance with an aspect, the efficacy of the model is increased. This involves separating a first set of cases from a second set of cases via the model. The first set of cases is associated with an uncertainty level which is low. The second set of cases is associated with an uncertainty level is high.

The present teachings include a computer system for assessing uncertainties. The computing device includes a processor and a memory, the memory bearing computer executable code. The executable code is configured to perform the steps of: receiving a plurality of cases; training a model; applying the model on the plurality of cases, wherein the plurality of cases is associated with respective cases; determining a level of uncertainty in the plurality of cases; wherein the level of uncertainty is with a predetermined range, wherein the predetermined range is between a lower acceptable limit and higher acceptable limit; in response to determining the level of uncertainty in the plurality of cases is within the predetermined range, implementing a first solution; and in response to determining the level of uncertainty in the plurality of cases is outside a predetermined range, implementing at least one additional solution.

In accordance with an aspect, a server is in communication with the computing device.

In accordance with an aspect, in response to determining the level of uncertainty in the plurality of cases is outside the predetermined range, a second solution is implemented.

In accordance with an aspect, the plurality of cases is selected from the group consisting of image data, text data, and any combination thereof.

In accordance with an aspect, the image data includes images interpreted according to BI-RADS and images examined for microcalcifications, breast arterial calcifications (BAC), and lesions.

In accordance with an aspect, training the model involves modifying the model by developing a training strategy and thereby reducing the level of uncertainty.

In accordance with an aspect, implementing the first solution and the additional solution occurs in at least one of: triage setting and an auto-populating setting for reporting an assessment each case of the plurality of cases.

The present teachings include a computer program product for assessing uncertainties. The computer program product comprises computer executable code embodied in a non-transitory computer readable medium. When executing on one or more computing devices, the non-transitory computer readable medium performs steps of: receiving a plurality of cases; training a model; applying the trained model on the plurality of cases; determining a level of uncertainty in the plurality of cases; wherein the level of uncertainty is with a predetermined range, wherein the predetermined range is between a lower acceptable limit and higher acceptable limit; in response to determining the level of uncertainty in the plurality of cases is within the predetermined range, implementing a first solution; and in response to determining the level of uncertainty in the plurality of cases is outside a predetermined range, implementing at least one additional solution.

In accordance with an aspect, the plurality of cases is selected from the group consisting of image data, text data, and any combination thereof.

In accordance with an aspect, the image data includes images interpreted according to BI-RADS and images examined for microcalcifications, breast arterial calcifications (BAC), and lesions.

In accordance with an aspect, implementing the first solution and the additional solution occurs in at least one of a triage setting and an auto-populating setting reporting for an assessment each case of the plurality of cases.

A second group of embodiments a method for assessing uncertainties is described. This method may be performed by a computer system that includes one or more computers. During operation, the computer system may receive information corresponding to medical imaging and clinical data for a plurality of individuals. Then, the computer system may apply a pretrained predictive model to the information for at least a subset of the plurality of individuals. Moreover, the computer system may determine levels of uncertainty in results of the pretrained predictive model for at least the subset of the plurality of individuals. Next, the computer system may dynamically adapt a lower acceptable limit and an upper acceptable limit that define at least one threshold range based at least in part on the determined levels of uncertainty and a predefined target performance of the pretrained predictive model for the plurality of individuals.

Furthermore, the computer system may perform a first remedial action for a first group of individuals in the plurality of individuals having the results where the levels of uncertainty are within the at least one threshold range. Alternatively, the computer system may perform a second remedial action for a second group of individuals in the plurality of individuals having the results where the levels of uncertainty are outside of the at least one threshold range.

Note that dynamically adapting the lower acceptable limit and the upper acceptable limit may be performed by a machine learning technique or a deep learning technique.

In some embodiments, the lower acceptable limit may be between 80 and 90% probability. Moreover, the upper acceptable limit may be greater than or equal to 95% probability.

Furthermore, the computer system may: receive second information corresponding to medical imaging and clinical data for a second plurality of individuals; and retrain the pretrained predictive model based at least in part on the second information.

Additionally, the computer system may train the predictive model based at least in part on a remainder of the plurality of individuals that excludes the subset of the plurality of individuals.

In some embodiments, performing the first remedial action may include: triaging individuals in the first group of individuals; and providing assessments associated with the individuals in the first group of individuals, where a given assessment is automatically populated based at least in part on triage results for a given individual in the first group of individuals.

Moreover, performing the second remedial action may include conducting a secondary review of the information for the second group of individuals by providing second information specifying the second group of individuals.

Note that the pretrained predictive model may include a neural network or a supervised machine-learning model.

Furthermore, the clinical data may include diagnostic information and/or electronic medical records.

Additionally, the medical images may include images interpreted according to BI-RADS and/or images examined for microcalcifications, breast arterial calcifications (BAC), and/or lesions.

In some embodiments, the plurality of individuals may include individuals having: a diagnosis of breast cancer, breast tissue having a type of density classification, and/or a diagnosis of cardiovascular disease.

Note that the predefined target performance may include an area under a receiver operator characteristic (AUC).

Another embodiment provides a computer-readable storage medium for use with the computer system. When executed by the computer system, this computer-readable storage medium causes the computer system to perform at least some of the aforementioned operations.

Another embodiment provides the computer system that performs at least some of the aforementioned operations. Notably, the computer system may include: a computing device; and memory coupled to the computing device, that stores program instructions, where, when executed by the computing device, the program instructions cause the computer system to perform at least some of the aforementioned operations.

These and other features, aspects, and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIGS. 4A-D depicts exemplary images for training the model and determining uncertainty.

Figure 4A:
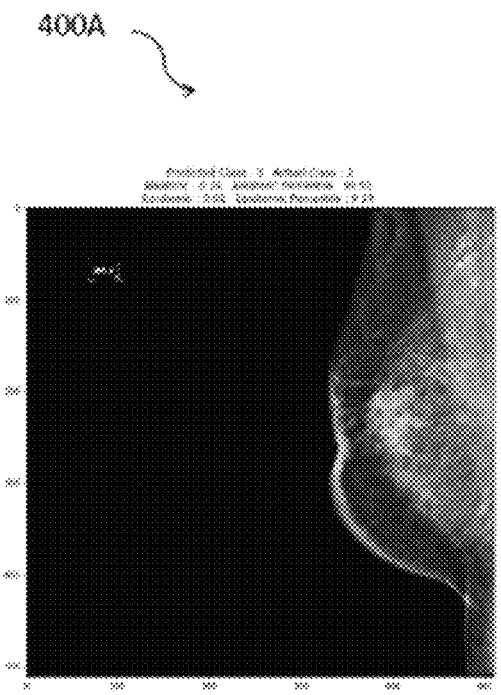
Figure 4B:
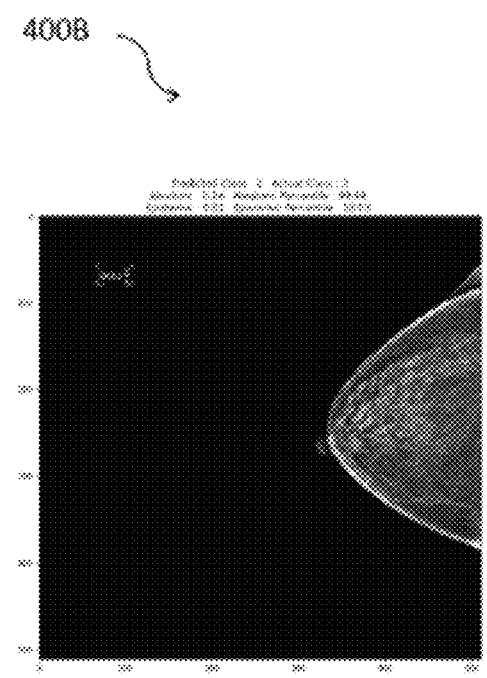
Figure 4C:
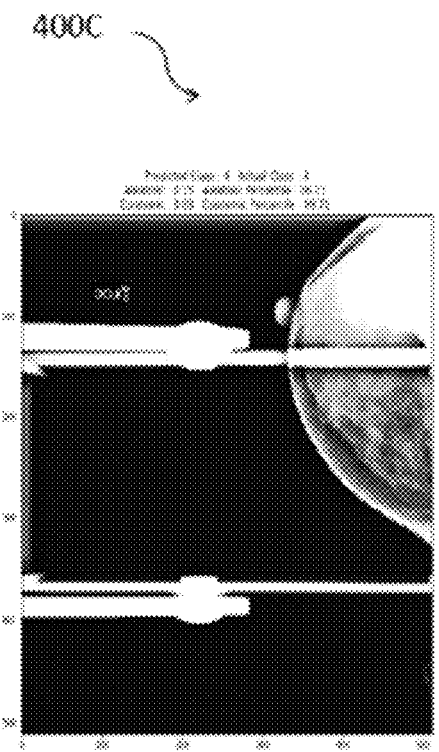
Figure 4D:
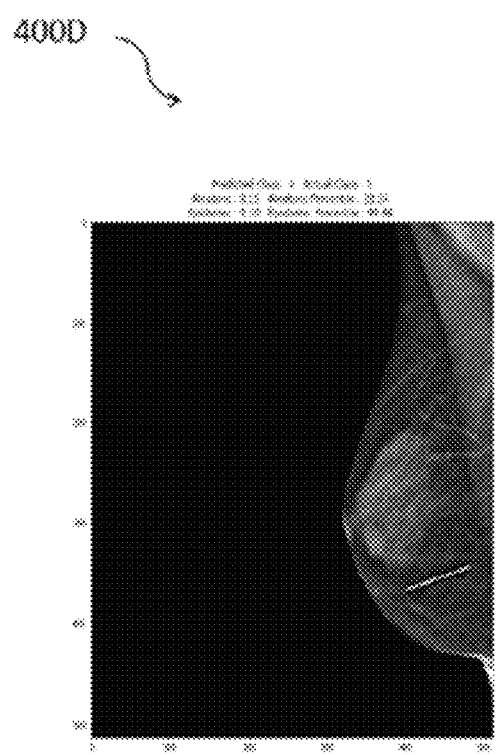
Figure 4E:
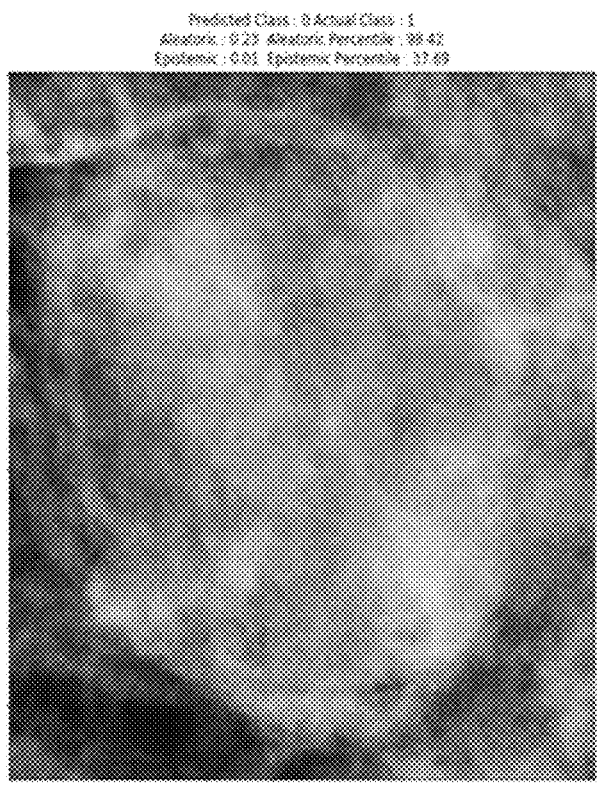
Figure 4F:

FIGS. 4E and 4F depicts exemplary images in the training set with high aleatoric uncertainty.

Figure 5:
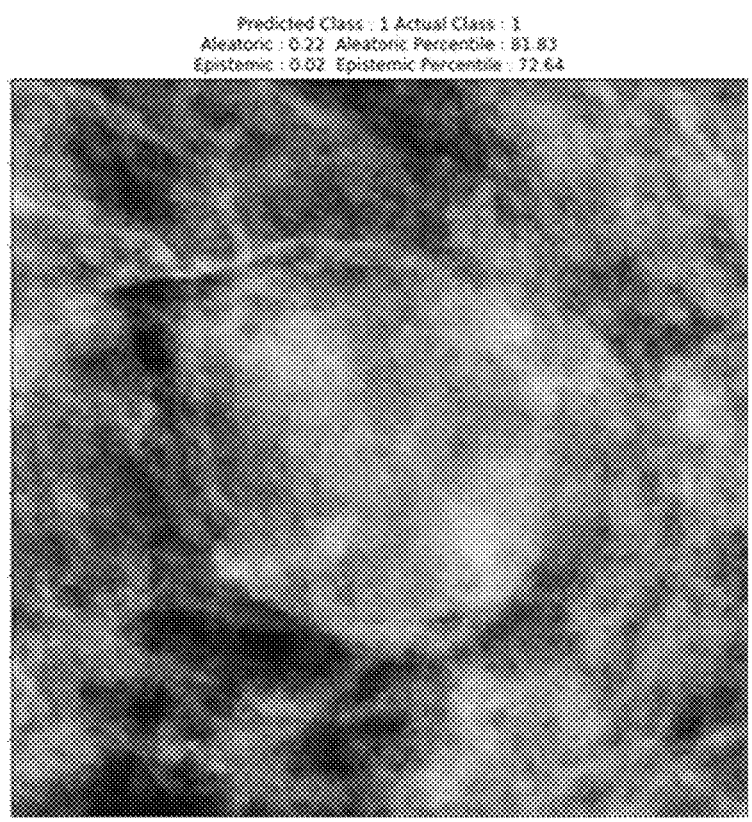

FIG. 5 depicts an example of a larger region of a surrounding breast for context when training a model.

Figure 6:
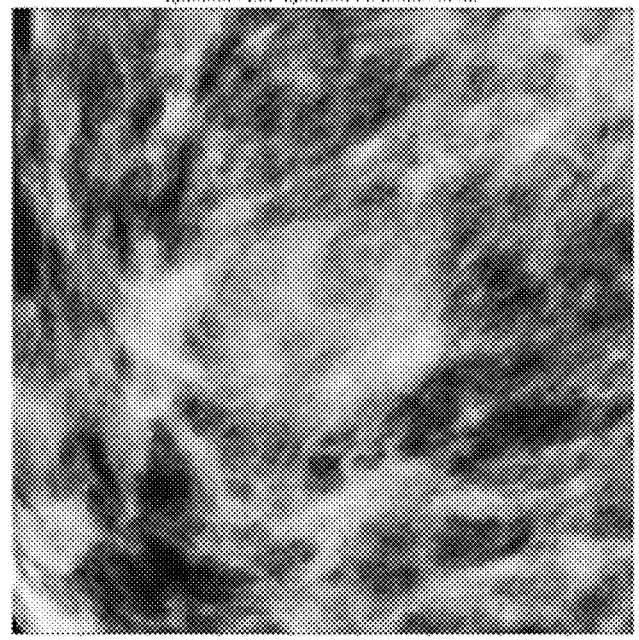

FIG. 6 depicts an example of the inclusion of larger surrounding breast tissue in the crop when training a model.

FIGS. 7A-C depicts exemplary images in the training with high epistemic uncertainty.

Figure 8:
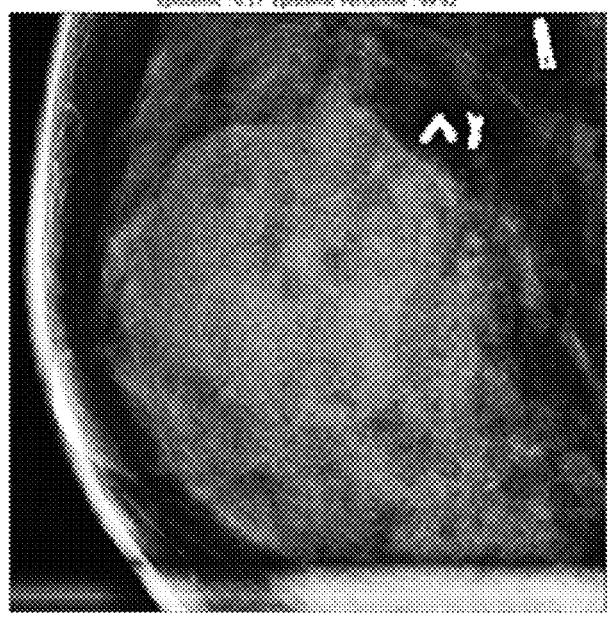

FIG. 8 depicts an example the increased crop size to improve a model.

Figure 9A:
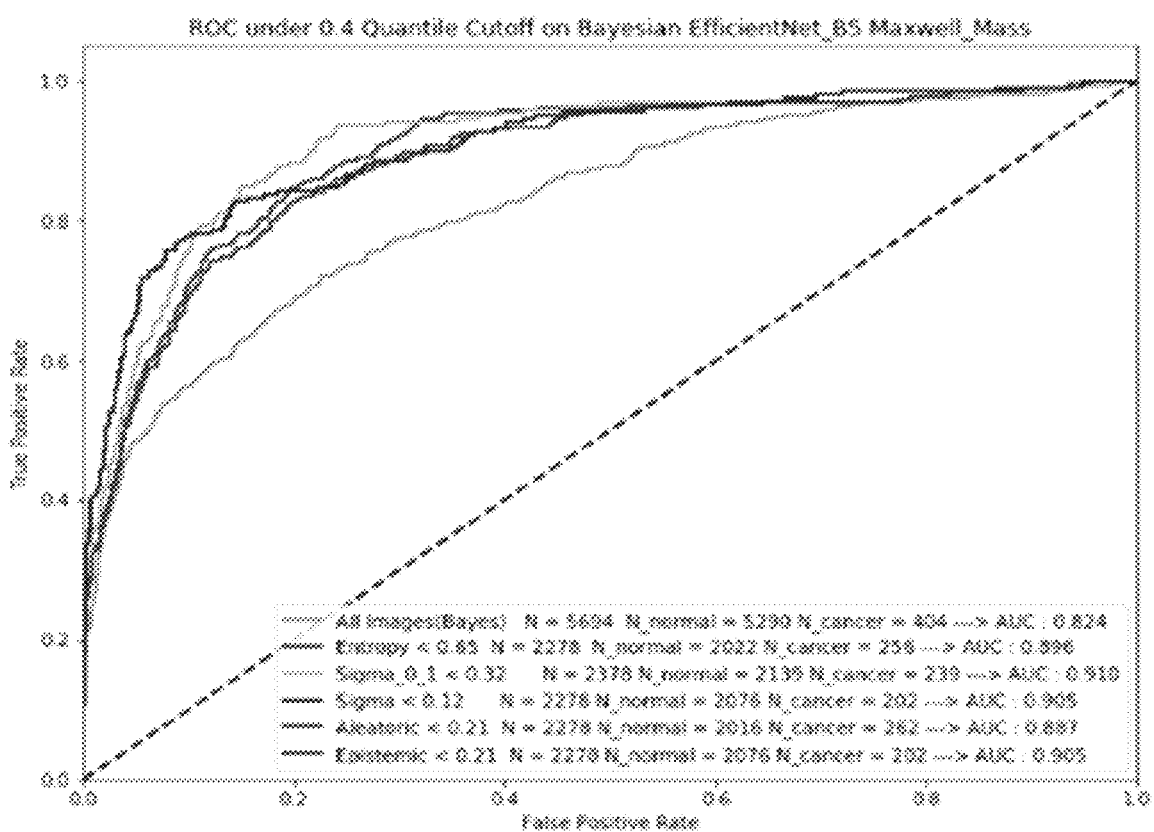
Figure 9B:
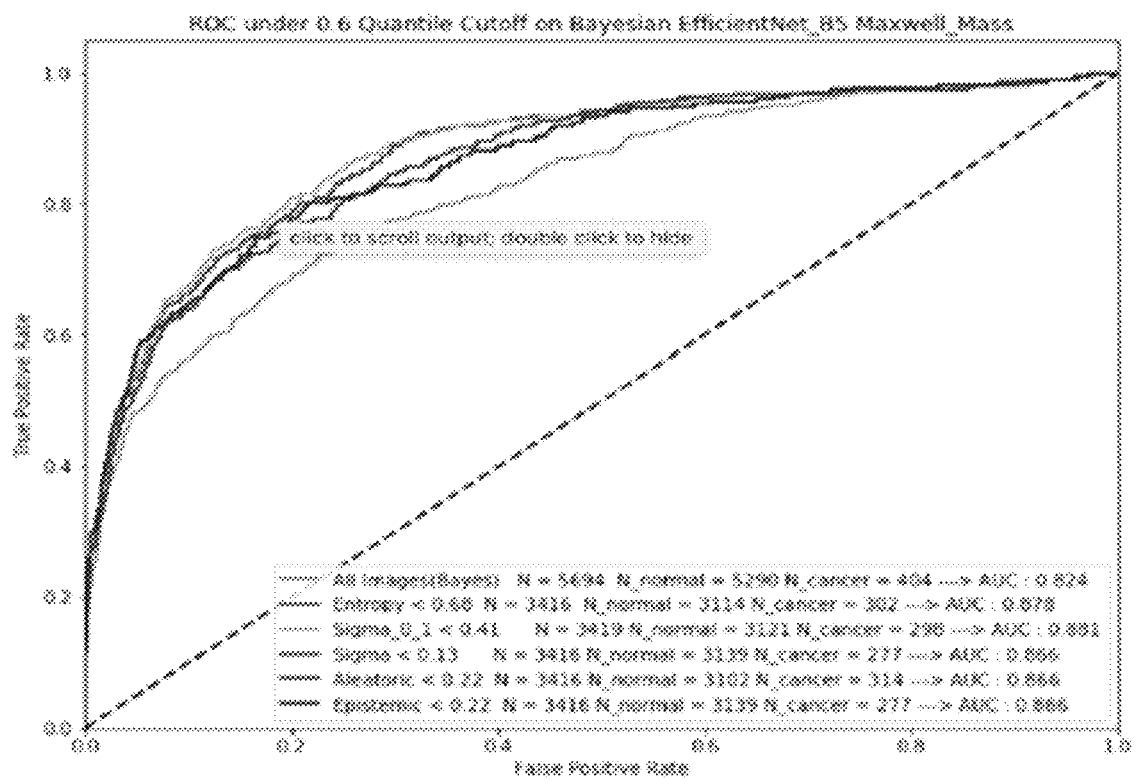
Figure 9C:
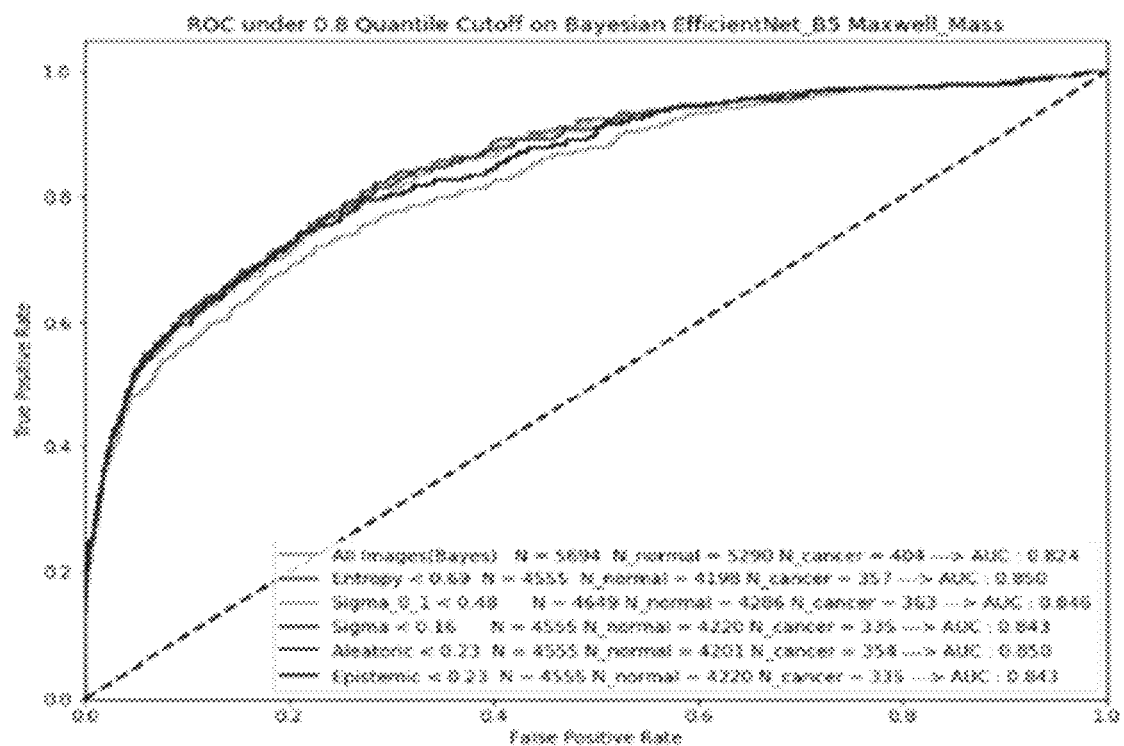

FIGS. 9A-C depicts an example of the efficacy of a Bayesian NN used with the systems and methods herein for cases of high and low levels of uncertainty.

Figure 10:
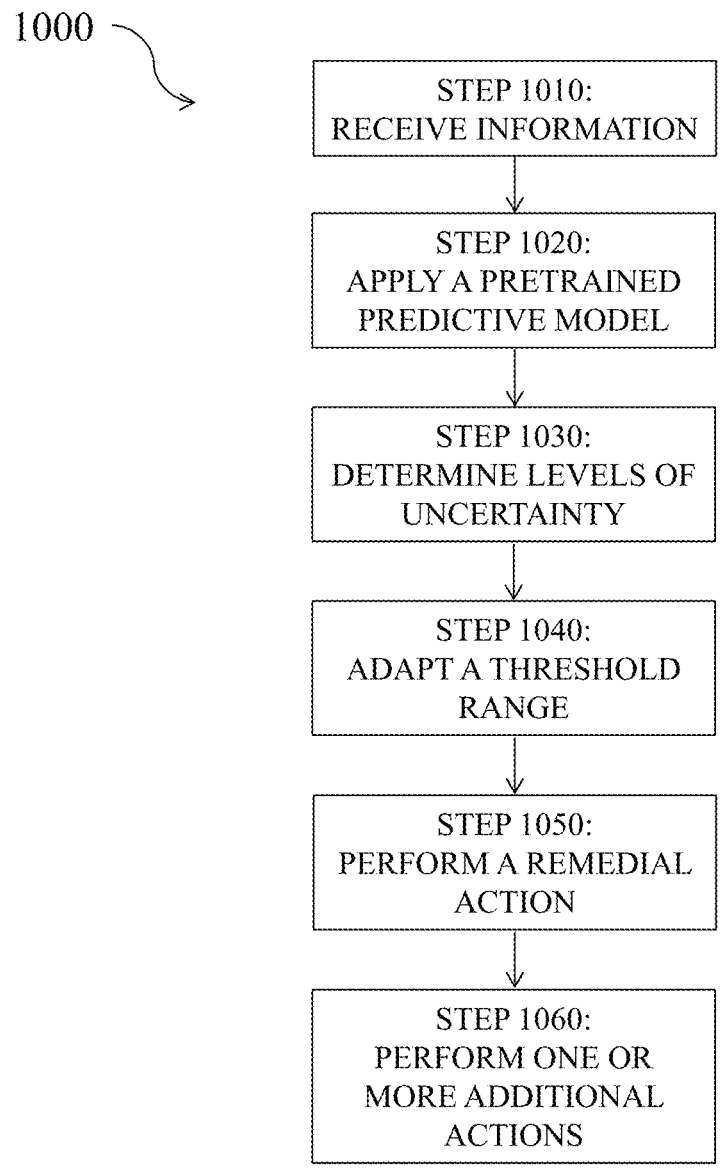

FIG. 10 depicts a flowchart of an example of a method for assessing uncertainties.

Figure 11:
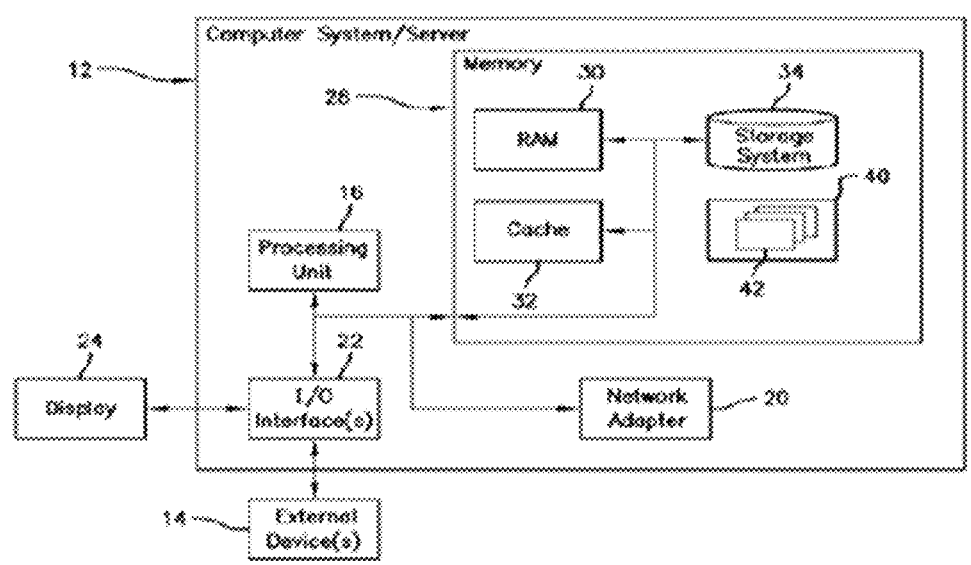

FIG. 11 depicts an exemplary computing device for implementing the systems and methods herein.

DETAILED DESCRIPTION

Abbreviations and Definitions

To facilitate understanding of the invention, a number of terms and abbreviations as used herein are defined below as follows:

Medical image: As used herein, the terms "medical image" generally refers to X-ray imaging, computerized tomography imaging (CT), magnetic resonance imaging (MM), positron emission tomography (PET), Digital Two-Dimensional (2D) imaging, Three-Dimensional (3D) Tomosynthesis, single-photon emission computed tomography (SPECT), ultrasound (US), endoscopy, thermography, medical photography, nuclear medicine functional imaging, elastography, photoacoustic imaging, echocardiography, functional near-infrared imaging, magnetic particle imaging, and the like.

BI-RADS®: As used herein, the term "BI-RADS®" refers to the standardized quality control system for interpreting mammograms, which was developed by the American College of Radiology. BI-RADS® Assessment Categories are: 0: Incomplete; 1: Negative; 2: Benign; 3: Probably benign; 4: Suspicious; 5: Highly suggestive of malignancy; and 6: Known biopsy—proven malignancy. The BI-RADS® atlas is available at http://www.acr.org.

Biopsy: As used herein, the term "biopsy" refers the removal of tissue from any part of the body or fluid for examination for disease. The tissue can be removed by fine-needle aspiration, core-needle biopsy, and surgical biopsy and subsequently examined under the microscope. The results of biopsy can be classified as benign and cancerous.

Breast Density: As used herein, the term "breast density" refers to categories, which a radiologist uses for describing a patient's mammogram. Breast density categories include Class A (or 1): Fatty; Class B (or 2): Scattered fibroglandular density; Class C (or 3): Heterogeneously dense; and Class D (or 4): Extremely dense.

DICOM®: As used herein, the term "DICOM®" refers to the international standard to transmit, store, retrieve, print, process, and display medical imaging information. A full description of the DICOM® standard and the association of Structured Reports with DICOM® images is provided in D. Clunie, "DICOM Structured Reporting," PixelMed Publishing, Bangor, Pennsylvania (2000); see also http://www.dicomstandard.org. Medical information associated with DICOM® and Structured Reports can be burned in, overlaid, or provided separate from the original image.

Machine learning: As used herein, the term "machine learning" refers to algorithms that build models based on training data, which are subsequently applied to perform specific tasks without using explicit instructions.

Deep learning: As used herein, the term "deep learning" is broadly defined to include machine learning which can be supervised, semi-supervised, or unsupervised. Architectures of deep learning include deep neural networks, deep belief networks, recurrent neural networks, and convolutional neural networks.

Deep neural network (DNN): As used herein, the term "deep neural network" is an artificial neural network with multiple layers between input and output layers. DNN model linear and non-linear relationships.

Prediction of Probability Distribution Function of Classifiers and Expressing the Results to a User Deep neural networks in the analysis of medical images and other complex data sets are used in the system and methods herein for prediction of probability distribution function of classifiers and expressing the results to the user.

In the systems and methods herein, the model outputs other parameters of the distribution function such as standard deviation in addition to the mean of the distribution (score) at each case. The standard deviation can be interpreted as the measure of uncertainty or confidence level. The determination of the uncertainty or confidence level is not limited to the distribution function. This enables the following capabilities, including but not limited to: (a) creating different protocols for cases where the model output predicts high uncertainty (low confidence); (b) identification of cases with large uncertainty for further examination and development of suitable training strategy to improve the trained model; and (c) creating a separate bucket for cases with high uncertainty in triage setting. For example, cases in the bucket of capabilities (c) may indicate more difficult cases which require additional diagnostics or follow up. In turn, the systems and methods herein perform the capabilities for: d) increasing the efficacy of the model by separating cases where the model is confident from cases which are uncertain; and e) creating a single score that takes into account other metrics of the distribution function rather than just its mean. For example, a score can include a combination of mean and variance such that: (i) the score for small variance is similar to the mean; and (ii) the score is reduced significantly for high variance.

Reference is made to the figures below to further describe the systems and methods herein.

Figure 1:
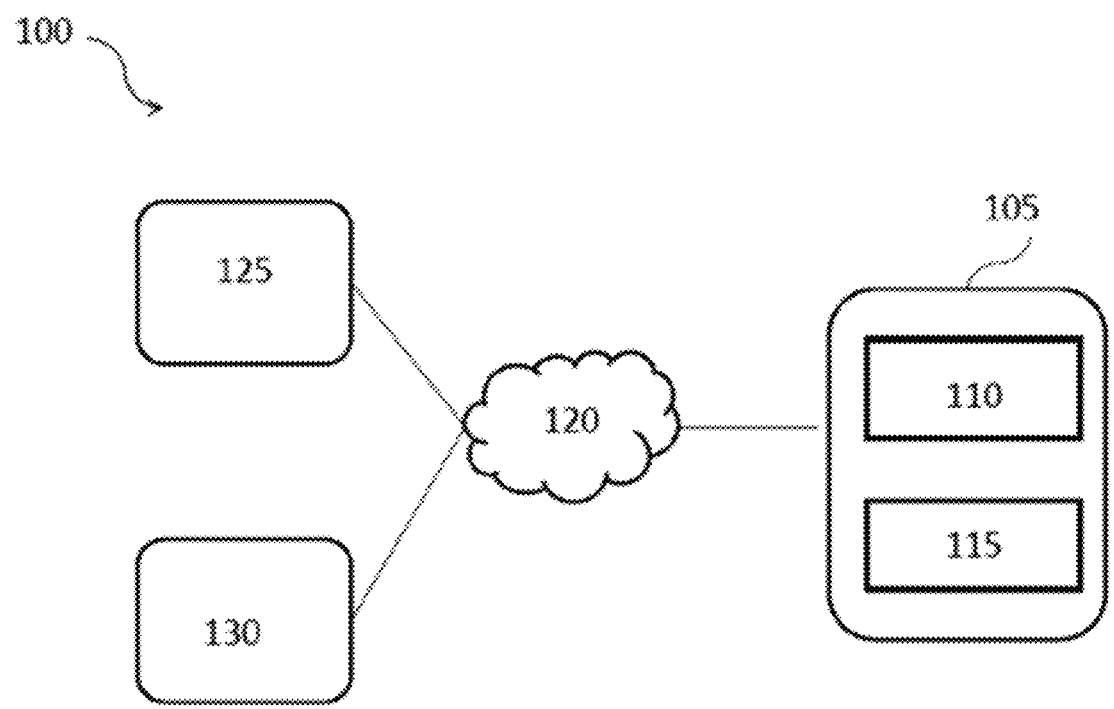
FIG. 1 depicts an exemplary computing environment for determining a score and uncertainty level of medical images.

Referring to FIG. 1, device 105 connects to training data set 125 and medical information 130 via network 120 in computing environment 100. Network 120 is a digital telecommunications network for sharing resources between nodes (i.e., computing devices). Data transmission between nodes is supported over physical connections (twisted pair and fiber-optic cables) and/or wireless connections (Wi-Fi, microwave transmission, and free-space optical communication). Device 105 may be any machine which is instructed to carry out sequences of arithmetic or logical operations via computer programming. Device 105 may include without limitation a Smartphone device, a tablet computer, a personal computer, a laptop computer, a terminal device, a cellular phone, and the like.

User Interface (UI) 110 and program 115 reside on device 105. UI 110 facilitates human-computer interaction which as a graphical user interface (GUI), which is composed of a tactile user interface and visual interface. UI 110 is connected to program 115 such that user of device 105 can interact with program 115 via graphical icons, audio indicators, and text-based user interfaces.

Program 115 receives data from training data set 125 and medical information 130. Based on the training data set 125, program 115 receives cases comprising medical images and other associated information (diagnosis, salient features of the medical images which lead to the diagnosis, and Digital Imaging and Communications in Medicine (DICOM) header). The DICOM header may contain a range of useful information including without limitation, the side (i.e., left or right), orientation, view, protocol, date of procedure, and so forth, many of which may be listed in a filename convention. This information may be extracted for use by the algorithm—for example, in order to compare results from multiple views, or from a time series of images. Examples of DICOM tags include without limitation: (a) pixel spacing (e.g., hex tag—(0028x,0030x)), which may be useful to scale the image in terms of real physical dimensions (e.g., mm), which can compute a 'Q factor' consistently; (b) diagnostic vs. screening (e.g., hex tag—(0032x, 1060x)), which may allow for inclusion or exclusion of diagnostic images from studies; and (c) patient orientation (e.g., hex tag—(0020x,0020x)), which may allow for displaying the images in a consistent manner. Stated another way, the images are displayed in the same orientation as used by radiologists in typical computer-aided design (CAD) systems. This can be advantageous when contour data is returned for display and/or analysis. For consistency in analysis, a predetermined orientation may be assigned (e.g., for mammograms—where the nipple points to the left in all images as is the industry standard).

From these medical images and other associated information, parameters are set for program 115 to create a model. The model implements an assessment protocol on data sets. More specifically, program 115 generates models by using training techniques: (A) ensemble learning; or (B) deep neural net architectures which use point estimates. The implemented assessment protocol can generate a score and determine a level of uncertainty by: (i) focusing on particular parameters; (ii) ignoring other parameters; and (iii) evaluating the significance (i.e., weight) of each parameter when. The score is associated with a probability of cancer or the degree of suspiciousness of a lesion in medical information 130.

Images with high levels of uncertainty can be sent to buckets for retraining. When retraining the model, the assessment protocol can be modified. In turn, this can increase the confidence level (i.e., reduce the uncertainty). When training the model, program 115 focuses on the perimeter of the organ captured and the overall appearance of the organs in the known medical images. The perimeter is focused on because certain spots are implicated with cancer risks. Medical images A and B do not have spots on the perimeter but the overall appearance of images A and B are noticeably different from known medical images used to train the model. Image A has surface ridges in the interior while the colorations are not obscuring the perimeter. Image B has colorations which obscure the perimeter, while being absent of the interior. The surface ridge in the interior and colorations are factors which are not initially understood and therefore images A and B are deemed as having high uncertainty. To understand the implications (if any) of the surface ridges and colorations, which increase the uncertainty levels, program 115 sends images A and B to a bucket for retraining.

By determining the level of uncertainty and retraining images with high levels of uncertainty, the confidence in the score is evaluated and thereby program 115 is providing a level of granularity when analyzing images and other data sets, while improving the models and implementing assessment protocol.

Stated another way, program 115 receives image data from medical information 130, wherein the image data are, for example, mammograms of a plurality of patients. In response to program 115 applying the implemented assessment protocol on the medical information 130, program 115 generates a score and level of uncertainty. The generated score and level of uncertainty are outputted to UI 110. The generated score on the medical image can be thought of as the mean of the probability distribution function (PDF). However, there are other metrics of the distribution function that are useful and provide more granularity into the model output. For example, a normal distribution is uniquely characterized by its mean and standard deviation. Standard deviation can be thought of as a measure of uncertainty of model output. As such, the systems and methods herein can be appended to not only include the score but details of the probability distribution function, including but not limited to a level of uncertainty, for each instance.

Program 115 applies machine learning techniques when assessing uncertainties in mammography. More specifically, program 115 accounts for aleatoric and epistemic parameters. Aleatoric parameters assess statistical uncertainty (i.e., stochastic variability in data), which is always present and thus not possible to eliminate with more data. Examples of aleatoric parameters as applied to mammography in the systems and methods herein include: (1) positioning/compression of breast; (2) variations in sensor efficiency or X-ray calibration; and (3) random seeds used to train or test models. Epistemic parameters assesses systematic uncertainty (i.e., missing knowledge due to limited data), which should decreases with more data and more precise instruments. Examples of epistemic parameters as applied to mammography in the systems and methods herein include: (4) spatial resolution of sensors; (5)

limited spatial views (typically 4 for 2D mammography and prior visits); (6) Image processing algorithms (presentation view)—different for each vendor; (7) architecture of neural network; (8) labels which are incorrect or missing; (9) rare cases with limited examples in training set; (10) random selection of women based on age, genetics, and breast density; and (11) inherent feature similarities between cancer and benign instances. Even seemingly "perfect" images (i.e., high resolutions images with well defined features) have limited information content. For example, some lesions are highly likely to be cancer (speculated masses), while many other lesions have much lower probability of being cancerous. More images cannot eliminate systematic uncertainty since the information pertaining to cancer versus benign is not available in a single image. Program 115 can use epistemic parameters, which may reduce uncertainty by considering prior images and carefully comparing right and left views. Otherwise, other modalities (ultra-sound, MM)—or biopsy are needed to complement the mammograms when program 115 assesses uncertainty. Epistemic uncertainty associated with examples 4-10 decreases as the quality of images increases, and program 115 acquires more data. However, uncertainties associated with example 10 may be large and are not possible to eliminate.

Program 115 uses machine learning techniques during anomaly detection during mammography and quantification of breast arterial calcifications (BAC). Regardless of the location of calcification, any calcification in the artery indicates the presence/onset of artery disease. As such, observation of BAC in mammogram has direct impact on the risk factor for, but not limited to, coronary heart disease (CHD), kidney disease, and stroke. Leading cause of CHD is due to plaque buildup, which can rupture or narrow the coronary artery, regardless of whether the plaque is calcified. Calcification is the last stage of plaque development. BAC may be an indicator of both calcified and non-calcified plaque in the coronary artery. Thus, presence of BAC increases the chance that a plaque will form, or is present, at another location, such as the heart. The use of uncertainty, as determined by program 115, enables more accurate detection and quantification of BAC which can in turn be used to calculate risk of CHD, stroke, and other diseases.

Figure 2:
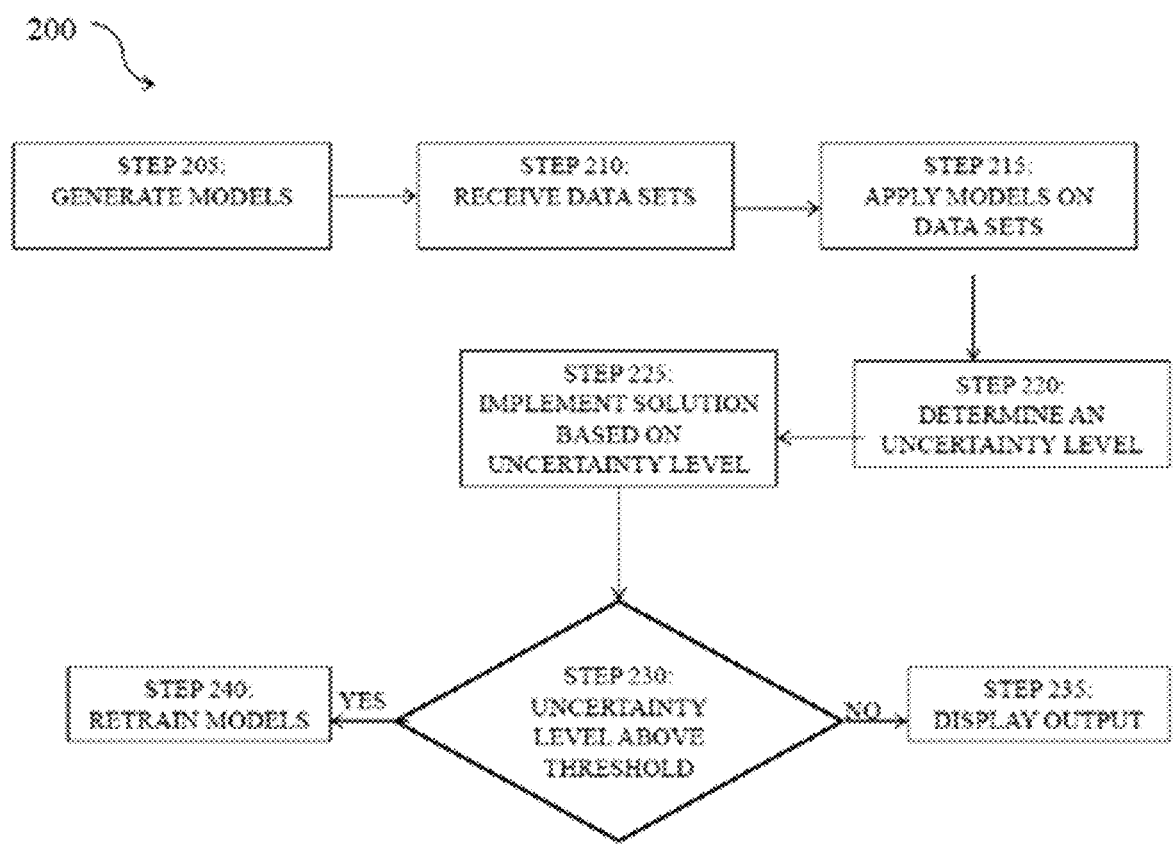
FIG. 2 depicts a flowchart of an example of a method for determining a score and uncertainty level of medical images.

In FIG. 2, program 115 performs the steps in flowchart 200. These steps determine a measure of uncertainty/confidence level as an output of the systems and methods herein.

In step 205, program 115 generates models in response to receiving the contents of training data set 125. Techniques A and B are machine learning techniques used by program 115 to generate models.

Technique A is based on ensemble learning and relies on the creation of several models that are maximally de-correlated but with similar efficacy. In practice, the models have some degree of correlation. At inference, program 115 runs the models for each instance and generates the corresponding probability distribution function which at the minimum may be the mean and variance. While Bayesian models used to generate probability distribution function are in technique A, the systems and methods herein can also apply to non-Bayesian models. When program 115 uses technique A, the variance in models are minimized such that the generated score is incorporated into model outputs which is accessible to an end user of program 115 in an actionable way.

Some non-Bayesian modeling techniques to create different models can be, but not limited to, one or combination of the following:
1. models chosen at different epochs in training;
2. models created based on different neural net architecture;
3. models created by using different initialization of the weights;
4. models created by different ways of combining the predictions;
5. models created by perturbing the trained weights;
6. models created by perturbing the input;
7. models created by using different training sets (e.g., bootstrap aggregating and bagging); and
8. models created by using different test sets (e.g., different cases of normal distribution and bootstrapping techniques for cancer detection).

Program 115 can also use deep neural networks (DNN) of technique B to generate models. DNN frameworks use point estimate for the weights in every node and also use non-probabilistic loss function. Since an objective of program 115 is to obtain the output in the form of a probability distribution function in general and estimates of the uncertainty in particular, program 115 can use the probability distribution over the weights, and/or loss function. The Bayesian neural nets have been partially incorporated into DNN frameworks, such as Pytorch and Tensorflow 2.0.

In step 210, program 115 receives data sets in medical information 130. A score and uncertainty levels of the data sets in medical information 130 are determined by the models applied by program 115.

In step 215, program 115 applies models on data sets in medical information 130. The applied models of program 115 use an assessment protocol to determine a similarity level to known examples of cancer. More specifically, the assessment protocol involves the application of autoencoder or tangent kernel of the classifier on medical information 130. Stated another way, the assessment protocol establishes a baseline for diagnoses (e.g., protrusions which are deemed as cancerous lesions or benign abnormalities) to aid in the evaluation of medical images. For example, the medical images often may have obscured lesions, which open up the possibility of false positives or false negatives. Program 115 can compare the incoming data sets from medical information 130 to the baseline and thereby finding similarities and differences. This is the basis for a similarity level. However, the evaluation does not end with similarities and differences. Based on the assessment protocol, as implemented by generated models, program 115 can focus on certain factors or ignore other factors to obtain a more granular, comprehensive, and accurate evaluation of the incoming data sets. Thus, the assessment protocol does not end the analysis with a yes or no answer (i.e., binary classification).

In step 220, program 115 determines uncertainty estimates for any ensemble classifier. In random forest (used as a binary classifier), each tree classifies the test cases as either belonging to class 0 or class 1. The binary prediction for tree I is $x_i$. The usual output that is further processed is the average of $x_i$, which is the averaging over all trees. This is the fraction of the trees which classified the case as being in class 1, and thus referred to as p.

In step 220, program 115 can also calculate the variance of $x_i$. Lower variance means better agreement among individual trees (lower uncertainty). Higher variance means the trees disagree more (high uncertainty).

Generally, program 115 can simply calculate the variance empirically for each test case. However, for special cases of RF (since each tree is a binary decision), the variance is a function of p where:

$$\mathrm{Var}(x_i) = p(1-p).$$

At the extremes p=0 or p=1, the uncertainty is zero since all trees have to agree to reach the extremes. At the midpoint where p=0.5, the uncertainty is a maximum.

Program 115 determines uncertainty measures via specific use cases when training the model. Thus, program 115 can be used for binary classification and non-binary classification. For example, the model may be trained for, but not limited to, density classification and biopsy. Breast tissue comprises milk glands, ducts, and dense and non-dense (fatty) breast tissue. In breast mammography, radiologists grade breast based on the density, using the BI-RADS reporting system. BI-RADS system is based on the proportion of dense to non-dense tissue, with score of 1 representing almost entirely fatty to 4 being extremely dense. However, there is significant intra-reader and inter-reader variability in assigning a BI-RADS score. This poses an issue with training neural net models for density classification since unlike biopsy confirmed cancer cases, there is no established convention for the density label. Stated another way, a breast originally assigned a density of 2 by radiologist A may be considered density of 3 by radiologist B. In addition, the images in mammography may have devices, markers, and other artifacts in them. A trained model may exhibit degraded performance if program 115 is not presented with enough such examples in the training set.

Program 115 may determine uncertainty such that variability and artifacts are addressed. More specifically, program 115 consider two uncertainties—aleatoric (irreducible) and epistemic (reducible). While epistemic uncertainty can be reduced with additional data, aleatoric uncertainty is due to inherent variation in the system such as reader dependent variations in the density BI-RADS score.

In examples of aleatoric uncertainty (fuzzy labels), program 115 uses a threshold above 99.5 percentile of aleatoric uncertainty to flag cases where the density labels may be: (i) less clear cut and (ii) borderline between neighboring density classes.

In examples of epistemic uncertainty (not having enough representation in the data), program 115 uses a threshold above 99.5 percentile of epistemic uncertainty to flag cases where either the model does not have enough examples similar to it in the training set and/or cases that should not be included in the training set.

In step 225, program 115 implements the solution based on the uncertainty level (as determined in step 220). Although techniques A and B are used to minimize the variance of the models and improve generalization, program 115 devises new resulting metrics which are (i) beyond the score that have not been incorporated into the model outputs or (ii) in a way to make it accessible to the user in an actionable way. The incorporation of the probability distribution over the loss function can be implemented. If the probability distribution is over the weights, program 115 runs the model multiple times to construct the probability distribution function.

In step 225, program 115 can use the uncertainty and other metrics of the probability distribution function as listed below. This list is not exhaustive and is meant only as illustration of diverse types of deployment:
  Risk assessment—risk mitigation strategies
  Lesion detection and classification
  Biopsy classifier
  Triage—create a separate bucket for cases with high uncertainty.
  Self-driving cars
  NLP/NLU
  Clinical assessment/decision support—care paths
  Sensor based system health monitoring—e.g., identification of atrial fibrillation
  Targeted retraining of models.

In step 230, program 115 determines if the uncertainty level is above a threshold associated with an acceptable level of uncertainty. Accordingly, if the threshold is exceeded, then program 115 proceeds to retrain the models in step 230. Stated another way, there may be models generated that do not have a high enough confidence level for program 115 to make accurate evaluations of medical information 130. More specifically, cases with high uncertainty levels are sent to a bucket and subsequently retrained. If the threshold is not exceeded, program 115 displays the output with the score to include other metrics (e.g., uncertainty and confidence level) that become available through techniques A and B in step 235. This indicates that the generated models have a high enough confidence level for program 115 to make accurate evaluations of medical information 130.

Figure 3:
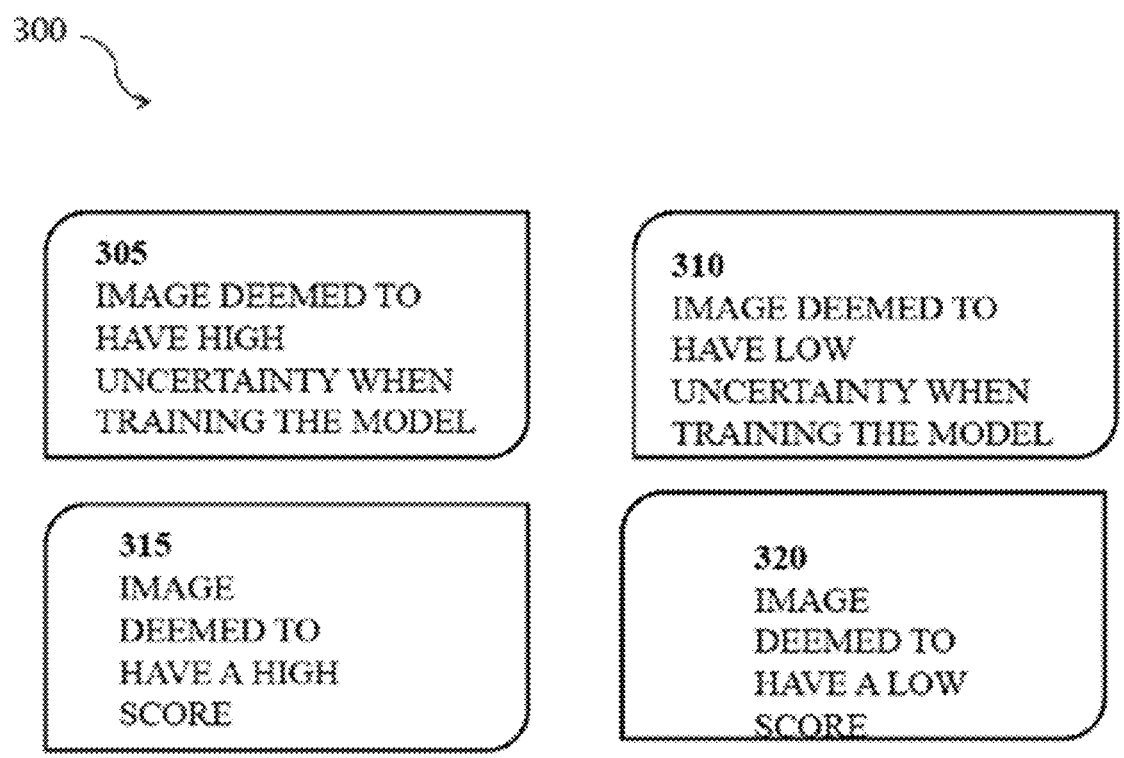
FIG. 3 depicts exemplary images analyzed and evaluated by the systems and methods herein when training the model.

Referring to FIG. 3, program 115 generates models using techniques A or B. Based on the models, the images are deemed to have a low uncertainty or high uncertainty. During the training of and generation of the model, program 115 receives images and accompanying information. Images 315 and 320 are cases of a high score and low score. Image 315 is absent of surface lesions that are clearly visible in image 320. In contrast, images 305 and 310 are not as straightforward for program 115 to analyze when training the model. Image 305 is deemed to have a high uncertainty, whereas image 310 is deemed to have low uncertainty. Program 115 can ascertain that: (i) images 315 and 320 have elements which decrease the probability of accurate and precise binary classification regions by noticing that: (a) image 305 appears obscure whereas (b) none of the regions of image 310 appear obscure; and (ii) images 315 and 320 are absent of elements which decrease the probability of accurate and precise binary classification.

Referring to FIGS. 4A-D, program 115 can identify cases with high uncertainty of one type, which had a low uncertainty of the other type. This further validates the utility of these two types of uncertainty and demonstrates that the two uncertainty measures are distinct, while measuring different types of uncertainty. If the two uncertainties been highly correlated, program 115 may have not been able distinguish the "fuzziness" of the labels in the training set from not having had sufficient examples of a particular type of image in the training set.

FIGS. 4A-D depicts examples of cases where the model predicted low uncertainty and examples with high uncertainty are depicted. Cases with high uncertainty are seen to be cases where the cancer is not as clearly evident in the image. One possible application of this new information about the model uncertainty is that one can devise a separate protocol for flagged cases where the model has high uncertainty (e.g., step 225). For example, such cases may indicate difficult cases that may need additional work ups and can be queued for ordering follow up diagnostic studies.

FIG. 4A shows an example from the training set where the original radiologist marked the image as density 2 while the model scored the image as density 3. Normally this case would count as a false positive by the model. Program 115 accounts for review A of a panel of radiologists of image 400A, whereby the consensus of review A is: (a) 50% confidence for a density of 2 and (b) 50% confidence for a density of 3. Program 115 applies the protocol, which accounts for review A of the panel, the model score, and original radiologist marking, on image 300A and thus deemed as having high aleatoric uncertainty (99.51 percentile). Stated another way, program 115 successfully flags image 400A as a borderline case, i.e., a case with high uncertainty, based on the scores of the original radiologist, model, and panel.

FIG. 4B shows an example from the training set where the original radiologist marked image 400B as a density of 3. However, program 115 scores image 400B with a density of 2. Normally, this case is counted as a false positive by the model. Program 115 accounts for review B of a panel of radiologists of image 400B, whereby the consensus of review B is classified with 100% confidence for a density of 2. Program 115 applies the protocol, which accounts for review B of the panel, the model score, the original radiologist marking, on image 400B and thus deemed as having high aleatoric uncertainty in this case (99.84 percentile). Stated another way, program 115 successfully flags image 400B as the wrong label. Accordingly, program 115 identifies wrongly labeled cases and subsequently corrects the label or removes the wrongly labeled cases from the training set. This improves the efficacy of the model and subsequently implemented protocol. In a specific instance, the subsequently implemented protocol by program 115 leads to improvement of the 4 class kappa from 0.82 to 0.85 and binary kappa from 0.92 to 0.96.

FIG. 4C depicts a nonstandard, magnification diagnostic view in image 400C. Due to the high epistemic uncertainty of image 400C, program 115 is flagged. The protocol, as applied on image 400C, program 115 determines image 400C is overly saturated. Such cases can be removed from the training set. Another application of this uncertainty is in running the model live at a client's site. Density classification by radiologists is based on examination of all of the screening images and then assigning one breast density score to the patient. The model can consider all images of a patient and form a consensus breast density score by discarding images that have high epistemic uncertainty. Thus, program 115 excludes images, such as image 400C, that should not be considered in the density classification.

FIG. 4D depicts another example in the training set which has an embedded artifact in image 400D. Program 115 analyzes image 400D and subsequently deemed as having high epistemic uncertainty. Program 115 flags image 400D as the implemented protocol notes there are very few of such images in the training set. In such instances, program 115 either: (i) finds similar examples to add to the training set, or (ii) eliminates the case from the training set.

Referring to FIGS. 4E and 4F, from aleatoric and epistemic uncertainty from a crop-level CNN training model for lesions program 115 can leverage uncertainty to improve the training of the models. High aleatoric uncertainty indicates cases where the model is not sure about the classification score since there are other examples in the data set that appear similar but have an opposite class. High epistemic uncertainty indicates cases where the model has not seen sufficient representation/examples in the training set. Initially, program 115 examines cases in the training set with high aleatoric uncertainty.

FIGS. 4E and 4F show two cases in the training set with high aleatoric uncertainty. FIG. 4E is a positive class that is misclassified as a negative class by the trained model, whereas FIG. 4F panel is a negative class that is correctly classified by the trained model. The visual similarities of the two crop level images in FIGS. 4E and 4F, one normal and one cancer, is indicative of the difficulty in distinguishing the correct class with high confidence for these two crops. Assessment of the suspiciousness of the lesions by radiologists relies on the examination of the entire breast and comparing all four views in screening setting in mammography. Assessment of suspiciousness of the lesion is significantly hampered for a human reader at crop level without the context of the entire breast. The tighter the crop, the less of a context the radiologist has to interpret the crop which reduces the probability of correctly classifying the crop. To test whether this is also true for the model, and as a remedy, program 115 extracts the same lesion but at a crop size that captures more of the surrounding breast area.

Referring to FIG. 5, the same crop is determined as the class 1 case in FIG. 4E, except FIG. 5 has a larger region of the surrounding breast for context. This additional context enables the model, as generated by program 115, to: (i) get the correct class in contrast to the model prediction of the wrong class in FIG. 4E, while (ii) significantly reducing aleatoric uncertainty also from 98.42 percentile to 81.83 percentile. This uncertainty can be further reduced if the models are trained by program 115 with crops at different crop size levels. This improves the training, whereby program 115 creates crops at different crop size levels and combines the scores of the crops, such methods such as majority voting or averaging the scores. This approach can be performed even without retraining the model. Another way of improving the model is to use different crop size levels as part of data augmentation. At the test stage, program 115 can run the model for different crop sizes and then creates a final score through such methods, but not limited to, majority voting or averaging the scores. Another way to improve the models, program 115 can feed crops at different crop size levels to a multi-scale convolution neural net. The epistemic uncertainty has increased in FIG. 5 as compared to that in FIG. 4E. This is attributed to the fact that the model was trained on tight crops and it has not seen many examples that contain as much surrounding breast tissue.

Referring to FIG. 6, the effect of program 115 trained model on the crop in FIG. 4F with class 0 but with the inclusion of a larger surrounding breast tissue in the crop is depicted. The aleatoric percentile is significantly reduced from 99.06 percentile to 35.95 percentile. Stated another way, the confidence level in score of the model is higher since it has more context for assessing the suspiciousness of the lesion. The epistemic percentile has increased, as expected since the model is trained on tight crops and the high epistemic uncertainty points to the fact that there are not many cases in the training set with such large segment of the surrounding tissue around a lesion like structure.

Referring to FIGS. 7A-C, several cases with high epistemic uncertainty in the training set are depicted. These are cases that despite providing the label in the training set, the model has difficulty learning the correct classification. FIGS. 7A-C are very unusual cases with scant representation in the training set. The high epistemic uncertainty indicates the need to include more such examples for the training set to improve the model. In FIG. 7A, the presence of large calcifications gives the impression of an oval mass with embedded calcifications. In FIG. 7B, there is a region of enhanced density with calcified breast artery. In FIG. 7C, there are surgical clips.

Referring to FIG. 8, program 115 increases the crop size to include more of the surrounding breast tissue, and this results in: (i) a decreases the aleatoric uncertainty from 58.19 to 30.14 percentile; and (ii) a match between the predicted class and the actual mass. This is consistent with program 115 improving the performance of the model when providing more context, as described with respect to FIGS. 4E and 4F. However, the epistemic uncertainty has slightly increased from 97.37 to 99.92 percentile. This is expected since the larger cropped image includes captures an additional surgical clip as well as the device (the white bar at the bottom of the image) used for magnification view in mammography. There are even fewer such cases in the training set that include both surgical markers and the device, which further explains the higher epistemic uncertainty.

Referring to FIGS. 9A-C, program 115 can use crops of cancer and normal/benign images extracted from 2D mammography to train a CNN one-class classifier. Program 115 has also used the same images to train a Bayesian NN. The advantage of the Bayesian NN in this case is that one gets a prediction of the uncertainty. FIGS. 9A-C show the efficacy of the Bayesian NN for (a) including all cases independent of their uncertainty; and (b) including only cases where the model is confident about its classification score.

Stated another way, cases with high uncertainty are not included in the evaluation of medical information 130. Thus, the model efficacy is improved when cases with high uncertainty are flagged and not included in the evaluation.

Three ROCs are shown where the change in AUC is compared to the full set of data as program 115 filters out cases based on uncertainty values. Different measures of uncertainty are applied by program 115. In Graph 900A, the ROC is under a 40-percent cutoff where program 115 keeps 40% of the cases for each uncertainty measure (each representing a separate curve). In Graph 900B, the ROC is under a 60-percent quantile cutoff where program 115 keeps 60% of the cases for each uncertainty measure (each representing a separate curve). In Graph 900C, the ROC is under an 80-percent cutoff where program 115 keeps 80% of the cases for each uncertainty measure (each representing a separate curve). For each of Graphs 900A-C, 5694 total cases are analyzed without program 115 and 5290 cases are normal and 404 cases are normal, which results in an area under the curve (AUC) of 0.824. Uncertainty is not accounted for when the AUC of 0.824 is obtained.

Different types of uncertainties are utilized by program 115: entropy, classification sigma, classification probability sigma, quantification of aleatoric, and epistemic uncertainty. Classification probability sigma refers to the sample standard deviation of classification probability score inferred by the model and is denoted as sigma in FIGS. 900A, 900B, and 900C. It is also possible to convert classification probability to threshold-based classification. As an example, using a threshold of 0.5 for binary classification, program 115 can convert classification probability to threshold-based classification and then acquire the corresponding sample standard deviation, referred to as sigma_0_1 in FIGS. 900A, 900B, and 900C. After obtaining different uncertainty measures across all the images in a study, a ranking for different types of uncertainty measures can be acquired within each uncertainty estimation, respectively. For example, the ranking of entropy can be computed across all the images. A "quantile filter" can then be deployed based on the ranking of specific uncertainty to enhance the performance of program 115. When an X quantile filter is applied for a specific kind of uncertainty, program 115 will exclude images with this specific kind of uncertainty above X*100 percentile. For example, a 0.4 quantile filter on entropy will let program 115 exclude images with entropy values above the 40 percentile. FIG. 900A, which shows application to detection of suspicious mass in breast mammography, demonstrates that when program 115 applies 0.4 quantile filter based on the 5 types of uncertainty separately, entropy, sigma_0_1, sigma, aleatoric uncertainty, and epistemic uncertainty, the cutoffs for each uncertainty measure are 0.65, 0.32, 0.12, 0.21, and 0.21, respectively. This results in AUCs of 0.896, 0.910, 0.905, 0.887, and 0.905, respectively which are all higher than the AUC of 0.824 for the inference on the full set of images. Note that different numbers of cancer cases are eliminated for each uncertainty type as indicated in the figure caption. FIG. 900B shows the resulting AUCs of AUC of 0.878, 0.881, 0.886, 0.866, and 0.866 if the quantile cut off is set to 0.6 which is still higher than the AUC of 0.824 for the full set but somewhat lower than the case when the quantile cutoff is set to 0.4. FIG. 900C demonstrates that when program 115 applies 0.8 quantile filter on the 5 types of uncertainty separately with the resulting AUCs of 0.850, 0.846, 0.843, 0.850, 0.843, respectively. The improvement in AUC over the full set of images is still significant but is the smallest among all three quantile filter. However, the number of cancer cases eliminated is also smaller than the other two quantiles. Thus program 115 demonstrates the viability of all 5 types of uncertainties in enhancing the efficacy of the model as measured by the AUC. The lower the quantile filter, the larger the improvement in the AUC. Thus, program 115 measures uncertainty is most useful for particular applications where the goal is to have the highest AUC while removing as few cases as possible.

EXAMPLES

Aspects of the present teachings may be further understood in light of the following examples, which should not be construed as limiting the scope of the present teachings in any way.

Example 1

In the first example, the systems and methods herein present a case in medical imaging where a prior from certain probabilistic continuous distribution is put on the weights of the traditional pointwise neural network model and thus make it a variational dense layer. A fully Bayesian convolutional network may also be possible to deploy but can be more difficult to train. While the full model pipeline for computer assisted design (CAD) in medical imaging can consist of several neural networks including an object detector network, the final output of CAD is currently a score. The focus here is to show how changing the model output from score (mean) to one where both the mean as well as the standard deviation (i.e., an uncertainty level) is provided improves the results. Program 115 can also explain how this additional information can be useful for the user (e.g., radiologist using device 105). As such, program 115 is not limited to CNN here is not limited to CNN. Thus, the systems and methods herein are generally applicable to all CAD applications and can be incorporated into all CAD pipelines.

Example 2

In the second example, program 115 uses an object detection neural network to assess the uncertainty of the model prediction. Unlike the previous example where the weights of the neural net are Bayesian, here program 115 uses a standard faster RCNN object detection network with pointwise weights where the loss function is replaced with the quantile regression loss function. In this implementation, program 115 creates different models from those of technique A and B by changing the alpha parameter which refers to the desired quantile. A quantile of 0.5 is equivalent to the median which is value obtained in the standard approach, based on minimizing the Mean Absolute Error. For example, FIGS. 5A-C shows the ROC for three values of alpha. The result shows the uncertainty of the model in different parts of the ROC.

Example 3

In the third example, program 115 supports a triage system connected to a Picture Archiving Retrieval System. It is impractical for a radiologist or program 115 to review each case in the training set, which can consist of tens or hundreds of thousands or even more images. To further complicate this issue, density classification by radiologists is done on standard 4 view screening images. DICOM tags usually, but not always, identify nonstandard views including magnification views where devices appear in the images.

There can also be images with biopsy clips, pacemaker, and other artifacts that can confuse the model unless there are a sufficient number of examples in the training set. Program 115 uses: (i) epistemic uncertainty to enable identification of all of the above cases; and (ii) retraining buckets (as described above). Thus program 115 may identify which: (i) images are indicative of abnormal medical conditions requiring immediate medical care (i.e., low uncertainty); (ii) images that require further analysis (i.e., high uncertainty); and (iii) retraining.

Example 4

In the fourth example, an anomaly in or on a tissue surface can be analyzed using program 115, which provides a suspicion code. That code can, in real-time, populate a user interface to alert the radiologist or technician of a suspicious anomaly in or on the tissue surface, thereby leading to an auto-populating setting. In the auto-populating setting, a notification result file may be reported and thus generated to include the suspicion code. The notification result file can be in the form of a portable document format (PDF), DICOM® SR, JSON, HTTP, HTTPS, HTML, REST, or other communication format in which a "Suspicious" or " " (blank) code may be transmitted in a FFDM, CIS, RIS, HIS, or the like. The transmission of the notification result file to the work station can be accomplished via a number of networks, whether encrypted or unencrypted, including the Internet, private networks, and telecommunications networks such as the Public Switched Telephone Network or cellular networks using third generation cellular technology (e.g., 3G or IMT-2000), fourth generation cellular technology (e.g., 4G, LTE, MT-Advanced, E-UTRA, etc.) or WiMax-Advanced (IEEE 802.16m)) and/or other technologies, including the forthcoming 5G network, a variety of corporate area, metropolitan area, campus or other local area networks, enterprise networks, any switches, routers, hubs, gateways, and the like that might be used to carry data among participants in the system.

Dynamic Adapting of One or More Acceptable Thresholds

FIG. 10 presents a flowchart of an example of a method 1000 for assessing uncertainties. This method may be performed by a computer system that includes one or more computers.

During operation, the computer system may receive information (step 1010) corresponding to medical imaging and clinical data for a plurality of individuals. Then, the computer system may apply a pretrained predictive model (step 1020) to the information for at least a subset of the plurality of individuals. Moreover, the computer system may determine levels of uncertainty (step 1020) in results of the pretrained predictive model for at least the subset of the plurality of individuals. Next, the computer system may dynamically adapt (step 1030) a lower acceptable limit and an upper acceptable limit that define at least one threshold range based at least in part on the determined levels of uncertainty and a predefined target performance of the pretrained predictive model for the plurality of individuals. Furthermore, the computer system may perform a first remedial action (step 1040) for a first group of individuals in the plurality of individuals having the results where the levels of uncertainty are within the at least one threshold range. Alternatively, the computer system may perform a second remedial action (step 1050) for a second group of individuals in the plurality of individuals having the results where the levels of uncertainty are outside of the at least one threshold range.

In some embodiments, the computer system optionally performs one or more additional operations (step 1060). For example, dynamically adapting the lower acceptable limit and the upper acceptable limit may be performed by a machine learning technique or a deep learning technique.

Note that the lower acceptable limit may be between 80 and 90% probability. Moreover, the upper acceptable limit may be greater than or equal to 95% probability.

Furthermore, the computer system may: receive second information corresponding to medical imaging and clinical data for a second plurality of individuals; and retrain the pretrained predictive model based at least in part on the second information.

Additionally, the computer system may train the predictive model based at least in part on a remainder of the plurality of individuals that excludes the subset of the plurality of individuals.

In some embodiments, performing the first remedial action may include: triaging (or assessing) individuals in the first group of individuals; and providing assessments associated with the individuals in the first group of individuals, where a given assessment is automatically populated based at least in part on triage results for a given individual in the first group of individuals.

Moreover, performing the second remedial action may include conducting a secondary review of the information for the second group of individuals by providing second information specifying the second group of individuals.

Note that the pretrained predictive model may include a neural network or a supervised machine-learning model (such as CART, LASSO, SVM, random forests, a Bayesian model, a linear model, a nonlinear model, etc.). In some embodiments, the pretrained predictive model may be a regression model or a classification model.

Furthermore, the clinical data may include diagnostic information and/or electronic medical records.

Additionally, the medical images may include images interpreted according to BI-RADS and/or images examined for microcalcifications, BAC, and/or lesions.

In some embodiments, the plurality of individuals may include individuals having: a diagnosis of breast cancer, breast tissue having a type of density classification, and/or a diagnosis of cardiovascular disease. However, the disclosed embodiments may be used with a wide variety of diseases, including: cancer, neurological disease, metabolic disease, an auto-immune disease, an inflammatory disease, etc. More generally, the disclosed embodiments may be used in conjunction with a human trait, which may include positive traits (such as longevity, athletic prowess or intelligence).

Note that the predefined target performance may include an AUC. However, in other embodiments, a wide variety of target performance metrics may be used, including: specificity, sensitivity or recall, precision, F1-score, p-value, accuracy, a confusion matrix, mean square error, mean absolute error, a receiver operator characteristic curve (ROC) and/or another performance metric (which may be determined from the ROC and/or the confusion matrix).

In some embodiments, any of the preceding methods may include fewer or additional operations (or steps), an order of the operations may be changed, an operation may be separated into two or more operations, and/or two or more operations may be combined into a single operation.

While the preceding discussion illustrated the disclosed assessment techniques with an upper acceptable limit and a lower acceptable limit in a threshold range, in other embodiments there may be a single threshold value. Thus, there may be a single cutoff or threshold instead of a lower bound and upper bound for a threshold range. For example, when there are two types of cases for inference having associated low uncertainty and high uncertainty, a single cutoff or threshold may be sufficient. In particular, in applications that are focused on inference (instead of training), the two types of uncertainty (low and high) and a single cutoff or threshold may be used. Alternatively, as described previously, when there is another uncertainty bucket value, such as mid uncertainty (which may be used for training), then there may be an upper acceptable limit and a lower acceptable limit in a threshold range. Similarly, when there is a confidence interval around an uncertainty value (such as 0.2 with a confidence interval window of 0.15 to 0.25), the disclosed assessment techniques may use an upper acceptable limit and a lower acceptable limit in a threshold range.

In some embodiments, note that uncertainty computed by the computer program can be used to initiate semi-supervised learning process. A dataset can be partitioned into different buckets arranged by the combination of aleatoric and epistemic uncertainty from lower uncertainty to higher uncertainty. Then, a model can be trained from partitioned data with lower uncertainty as a teacher model. Such a model in nature may suffer less from noise caused by out of distribution datapoints, outliers as well as noisy ground truth. Next, a teacher model may be used to provide pseudo ground truth to the partitioned data with relatively higher uncertainty and these data will be combined with data that are partitioned in the lower uncertainty bucket. Retraining may be initiated to get the new teacher model. This process may continue until the last bucket of data is reached and processed.

Additional Examples

Breast Cancer:

A trained Bayesian predictive model may generate estimates for aleatoric and epistemic uncertainty for a subset of the plurality of individuals. A cutoff or threshold may be selected based at least in part on aleatoric or/and epistemic uncertainty quantification when the performance of remaining plurality of individuals reaches desired performance metrics as quantified by precision-recall curve or AUC in a ROC. In order to achieve statistical sufficiency, bootstrapping techniques may be used to determine the confidence interval of the uncertainty cutoff. For detection of suspicious lesions in mammography, in order to achieve an AUC of 0.85, a 95% confidence interval for the cutoff for the aleatoric uncertainty may be between 0.19 and 0.21. However, with improvements with our models stemming from updated techniques or new training examples, or deployment of our models for a different population, the AUC may change and so will the uncertainty interval or threshold range. Thus, in other embodiments, different numerical values may be used. It is also possible to define different uncertainty intervals for each operation point.

In this example, for the first remedial action, the model may be used in a triage setting. Notably, cases having an uncertainty from 0 to the lower bound of the uncertainty threshold or threshold range may be triaged based at least in part on their corresponding suspiciousness classification score. For example, a radiologist may prefer to focus on the suspicious cases first because those may require a quicker response and follow up. Ranking based at least in part on the suspiciousness classification enables this functionality.

Alternatively, for the second remedial action, for images with aleatoric uncertainty above the lower bound of the uncertainty threshold or threshold range (or, alternatively, within the threshold range), the ranking of cases based at least in part on their suspiciousness classification score may not be as reliable. Consequently, these cases may be flagged for more immediate review by radiologists or flagged for double read or could be flagged for follow up with patients.

Density Categorization:

A reference library approach may be used in conjunction with uncertainty. Notably, a trained Bayesian predictive model may first generate uncertainty quantification for the images. Low aleatoric uncertainty images may be reviewed additionally by internal experts to create the reference library for the downstream prediction tasks. An uncertainty score based at least in part on average angular similarity between the latent representations of the image of interest against the top-N (such as the top-20) most similar images in the reference library may be computed. In order to select the cutoff, the same process as in the preceding example may be used. In particular, a desired performance level may be set, and bootstrapping may be performed to get the confidence interval of the uncertainty cutoff (or the threshold range) when the performance of remaining images reaches the desired level. For density categorization, in order to reach a linearly weighted kappa of 0.9, an interval of angle 6.2° to 6.8° may be selected. The angle intervals may be adapted when more patients' images become available or the desired performance metrics changed.

In this example, for the first remedial action, for an image that has average angle from 0 to the lower bound of the uncertainty angle threshold (or threshold range), the Bayesian predictive model may be more confident in its prediction and the classification result may be kept. Alternatively, for the second remedial action, if the image has an average angle above the lower bound of the uncertainty angle threshold (or, alternatively, within the threshold range), the classification density may be upgraded to the next density level in order to reduce false omission risk.

In some embodiments of the assessment techniques, the uncertainty thresholds may be dynamically adapted based at least in part on the determined levels of uncertainty and a predefined target performance of the pretrained predictive model for the plurality of individuals. Additionally, the uncertainty thresholds may be dynamically adapted using an incremental/online learning-based approach. Notably, the model thresholds may be dynamically updated based at least in part on real-time feedback from radiologists on the cases in both the first and second remedial action buckets, as well as by the sequential addition of new cases, thereby accounting for plausible concept drift.

Breast Arterial Calcification and Cardiovascular Risk:

Uncertainty can be employed in the BAC detection. The process of quantifying BAC may use object detection (e.g., a region-based convolutional neural network or RCNN) to detect BAC and then quantifying the BAC present in those detections. A trained Bayesian predictive model may be used along with an object detection neural net (such as a faster RCNN) in order to quantify the uncertainty of each detection. For example, this can be done by augmenting the prediction layers/box estimation layers with Bayesian layers to get uncertainty. The uncertainty for an image can then be calculated by accumulating the uncertainties over individual detections. Thus, at the end, the model can provide the quantification of BAC along with its uncertainty. For detection of BAC in mammography, in order to achieve an AUC of 0.95, a cutoff for the aleatoric uncertainty of between 0.15 and 0.2 may be used. However, different uncertainty intervals may be used based at least in part on the clinical data. Notably, it has been empirically demonstrated that patients below the age of 40 have low BAC. Consequently, detections on a patient aged less than 40 with an uncertainty above a threshold of 0.8 may be rejected. Moreover, the thresholds may be adapted as more train-test data becomes available.

Cardiovascular Disease:

Cardiovascular risk for patients may be given by various calculators such as Pooled Cohorts Equation (PCE), Framingham Risk calculator etc. Notably, PCE 10-year ASCVD risk: 0-4.9% is low risk; 5 to 7.4% is borderline risk; 7.5-20% is intermediate risk; and greater than 20% is high risk. Each risk calculator has its own advantages and disadvantages. For example, they overestimate or underestimate risk for different patient age groups and ethnicities. Patients are typically advised to go on different treatments based at least in part on their risk and diagnosis by physicians. A trained uncertainty model may be employed that provides an uncertainty of the risk based at least in part on an individual patient's health characteristics. This may allow patients to be categorize based at least in part on their risk factors as well as the uncertainty. Thus, uncertainty measures across each risk group may be defined, and a tighter uncertainty interval may be used for the intermediate/high-risk population. Note that the uncertainty interval may depend on various characteristics of the population, such as age, ethnicity, sex etc. Patients with low uncertainty (e.g., within an uncertainty interval between 0.1 and 0.2) with both low and high cardiovascular risk can be accurately identified without further testing. In some embodiments, the uncertainty intervals may change depending on the target population, and improvements on the uncertainty prediction models.

In this example, for the first remedial action, the model may be used in a triage setting. Notably, cases that have high BAC quantification and low uncertainty may be flagged or highlighted because these are the cases where the model has high confidence in its predictions and high BAC quantification corresponds to higher cardiovascular risk. Alternatively, for the second remedial action, underestimating or overestimating cardiovascular risks can have serious consequences for the health of patients. Consequently, patients that have high uncertainty may be identified, and flagged because the model was not able to estimate the risk with good confidence. These patients may need to be re-evaluated for their risk using other tests, such as a stress test, CAC Agatson Scoring, etc.

While the preceding discussion illustrated the assessment techniques with particular numerical values, this is for purposes of illustration. In other embodiments, different numerical values and/or ranges of numerical values may be used.

As shown in FIG. 11, computer system/server 12 in computing node 1100 is shown in the form of a general-purpose computing device. The components of computer system/server 12 may include, but are not limited to, one or more processors or processing units 16, a system memory 28, and a bus 18 that couples various system components including system memory 28 to processor 16. In some embodiments, a computing device in the computing node 1000 may include: a processor (such as a multi-core processor or a multi-threaded processor), an ASIC, an FPGA, a graphics processing unit (GPU) or another type of computing device.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating systems, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical applications, or technical improvement over technologies found in the marketplace, or to enable others of ordinary skill in the art to understand the embodiments disclosed herein.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for assessing uncertainties, the method comprising:
by a computer system:
receiving information corresponding to medical imaging and clinical data for a plurality of individuals;
applying a pretrained predictive model to the information for at least a subset of the plurality of individuals;
determining levels of uncertainty in results of the pretrained predictive model for at least the subset of the plurality of individuals;
dynamically adapting a lower acceptable limit and an upper acceptable limit that define at least one threshold range based at least in part on the determined levels of uncertainty and a predefined target performance of the pretrained predictive model for the plurality of individuals;
performing a first remedial action for a first group of individuals in the plurality of individuals having the results where the levels of uncertainty are within the at least one threshold range; and
performing a second remedial action for a second group of individuals in the plurality of individuals having the results where the levels of uncertainty are outside of the at least one threshold range.

2. The method of claim 1, wherein dynamically adapting the lower acceptable limit and the upper acceptable limit is performed by a machine learning technique or a deep learning technique.

3. The method of claim 1, wherein the lower acceptable limit is between 80 and 90% probability.

4. The method of claim 1, wherein the upper acceptable limit is greater than or equal to 95% probability.

5. The method of claim 1, wherein the method comprises:
receiving second information corresponding to medical imaging and clinical data for a second plurality of individuals; and
retraining the pretrained predictive model based at least in part on the second information.

6. The method of claim 1, wherein the method comprises training the predictive model based at least in part on a remainder of the plurality of individuals that excludes the subset of the plurality of individuals.

7. The method of claim 1, wherein performing the first remedial action comprises:
triaging individuals in the first group of individuals; and
providing assessments associated with the individuals in the first group of individuals, wherein a given assessment is automatically populated based at least in part on triage results for a given individual in the first group of individuals.

8. The method of claim 1, wherein performing the second remedial action comprises conducting a secondary review of the information for the second group of individuals by providing second information specifying the second group of individuals.

9. The method of claim 1, wherein the pretrained predictive model comprises a neural network or a supervised machine-learning model.

10. The method of claim 1, wherein the clinical data comprises diagnostic information, electronic medical records or both.

11. The method of claim 1, wherein the medical images comprise images interpreted according to BI-RADS and images examined for microcalcifications, breast arterial calcifications (BAC), and lesions.

12. The method of claim 1, wherein the plurality of individuals comprise individuals having: a diagnosis of breast cancer, breast tissue having a type of density classification, or a diagnosis of cardiovascular disease.

13. The method of claim 1, wherein the predefined target performance comprises an area under a receiver operator characteristic (AUC).

14. A computer system, comprising:
a computing device; and
memory coupled to the computing device, wherein, when executed by the computing device, the computer system performs operations comprising:
receiving information corresponding to medical imaging and clinical data for a plurality of individuals;
applying a pretrained predictive model to the information for at least a subset of the plurality of individuals;
determining levels of uncertainty in results of the pretrained predictive model for at least the subset of the plurality of individuals;
dynamically adapting a lower acceptable limit and an upper acceptable limit that define at least one threshold range based at least in part on the determined levels of uncertainty and a predefined target performance of the pretrained predictive model for the plurality of individuals;
performing a first remedial action for a first group of individuals in the plurality of individuals having the results where the levels of uncertainty are within the at least one threshold range; and
performing a second remedial action for a second group of individuals in the plurality of individuals having the results where the levels of uncertainty are outside of the at least one threshold range.

15. The computer system of claim 14, wherein performing the first remedial action comprises:
   triaging individuals in the first group of individuals; and
   providing assessments associated with the individuals in the first group of individuals, wherein a given assessment is automatically populated based at least in part on triage results for a given individual in the first group of individuals.

16. The computer system of claim 14, wherein performing the second remedial action comprises conducting a secondary review of the information for the second group of individuals by providing second information specifying the second group of individuals.

17. The computer system of claim 14, wherein the predefined target performance comprises an area under a receiver operator characteristic (AUC).

18. A non-transitory computer-readable storage medium for use in conjunction with a computer system, the non-transitory computer-readable storage medium configured to store program instructions that, when executed by the computer system, causes the computer system to perform operations comprising:
   receiving information corresponding to medical imaging and clinical data for a plurality of individuals;
   applying a pretrained predictive model to the information for at least a subset of the plurality of individuals;
   determining levels of uncertainty in results of the pretrained predictive model for at least the subset of the plurality of individuals;
   dynamically adapting a lower acceptable limit and an upper acceptable limit that define at least one threshold range based at least in part on the determined levels of uncertainty and a predefined target performance of the pretrained predictive model for the plurality of individuals; performing a first remedial action for a first group of individuals in the plurality of individuals having the results where the levels of uncertainty are within the at least one threshold range; and
   performing a second remedial action for a second group of individuals in the plurality of individuals having the results where the levels of uncertainty are outside of the at least one threshold range.

19. The computer program product of claim 18, wherein performing the first remedial action comprises:
   triaging individuals in the first group of individuals; and
   providing assessments associated with the individuals in the first group of individuals, wherein a given assessment is automatically populated based at least in part on triage results for a given individual in the first group of individuals; and
   wherein performing the second remedial action comprises conducting a secondary review of the information for the second group of individuals by providing second information specifying the second group of individuals.

20. The computer program product of claim 18, wherein the predefined target performance comprises an area under a receiver operator characteristic (AUC).

* * * * *